United States Patent [19]

Rossy et al.

[11] 4,143,050

[45] Mar. 6, 1979

[54] MANUFACTURE OF 3-HALOSULFONYLTHIOPHENE-CARBOXYLIC ACID COMPOUNDS

[75] Inventors: Phillip A. Rossy, Ludwigshafen; Werner Hoffmann, Neuhofen; Norbert Mueller, Mutterstadt, all of Fed. Rep. of Germany

[73] Assignee: BASF Aktiengesellschaft, Ludwigshafen, Fed. Rep. of Germany

[21] Appl. No.: 863,913

[22] Filed: Dec. 23, 1977

[30] Foreign Application Priority Data

Jan. 5, 1977 [DE] Fed. Rep. of Germany ....... 2700261
Apr. 20, 1977 [DE] Fed. Rep. of Germany ....... 2717477

[51] Int. Cl.$^2$ .......................................... C07D 333/24
[52] U.S. Cl. ........................ 260/332.2 C; 260/329 S; 424/275
[58] Field of Search ................... 260/332.2 C

[56] References Cited

U.S. PATENT DOCUMENTS 4,028,373  6/1977  Hromatka et al. ............... 260/329 S

*Primary Examiner*—Gerald A. Schwartz
*Attorney, Agent, or Firm*—Keil & Witherspoon

[57] ABSTRACT

3-Halosulfonylthiophene-carboxylic acid compounds are manufactured by reacting 3-ketothiophane-carboxylic acid compounds with sulfonic acid compounds, reacting the end product from the 1st reaction stage with alkali metal polysulfides, reacting the end product from the 2nd stage with a dehydrogenating agent and finally reacting the end product from the 3rd stage with halogen and water. The products are starting compounds for the manufacture of drugs, dyes and crop protection agents and have an anti-inflammatory, analgesic and anti-rheumatic action. In particular, the end products I are starting materials for the manufacture of sweeteners which are non-toxic and free from an after-taste, flavor-improving agents, diabetic aids and feedstuffs, and provide the means of a simple and economical synthesis of thiophene-saccharins.

14 Claims, No Drawings

MANUFACTURE OF 3-HALOSULFONYLTHIOPHENE-CARBOXYLIC ACID COMPOUNDS

The present invention relates to a new process for the manufacture of 3-halosulfonylthiophene-carboxylic acid compounds by reacting 3-ketothiophane-carboxylic acid compounds with sulfonic acid compounds, reacting the end product from the 1st reaction stage with alkali metal polysulfides, reacting the end product from the 2nd stage with dehydrogenating agents and finally reacting the end product from the 3rd stage with halogen and water.

German Laid-Open Application DOS No. 2,534,689 discloses the reaction of 3-ketothiophane-4-carboxylic acid methyl ester with phosphorus pentachloride to give 3-chlorothiophene-4-carboxylic acid chloride and the conversion of the 4-carboxylic acid compound, obtained from the chloride by hydrolysis, to the potassium salt of 3-sulfothiophene-4-carboxylic acid by the use of copper-I chloride with sodium bisulfite, sodium hydroxide solution and potassium chloride. The acid is next produced from the potassium salt by treatment with acid ion exchangers and is esterified by refluxing with methanol; the ester formed is refluxed with thionyl chloride for 16 hours and thus converted to 3-chlorosulfonylthiophene-4-carboxylic acid methyl ester. German Laid-Open Application DOS No. 2,537,070 discloses a similar reaction entailing numerous stages.

The chlorosulfonylthiophene-4-carboxylic acid ester obtained can be converted to the 3-sulfonamide by means of ammonia, and the 3-sulfonamide can be hydrolyzed to give 3-sulfamoylthiophene-4-carboxylic acid; cyclization, for example with polyphosphoric acid, gives 2,3-dihydro-3-oxo-thieno[3,4-d]isothiazole-1,1-dioxide (thiophene-saccharin).

2,3-Dihydro-3-oxothieno[2,3-d]-isothiazole-1,1-dioxide, another thiophene-saccharin, can be prepared by a similar method.

Amongst the chemical compounds suitable for use as sweeteners, only very few have found use in practice, and amongst these none simultaneously fulfil the 3 requirements of high sweetening power, non-toxicity, and absence of a savor or after-taste. The above thienosaccharins are acid compounds which are used as sweeteners as such or in particular in the form of their equally non-toxic salts. The salts can be manufactured in accordance with conventional methods by reaction with suitable organic or inorganic bases appropriate for the manufacture of the non-toxic salts usable as sweeteners; the bases used are preferably alkali metal hydroxides, e.g. sodium hydroxide or potassium hydroxide, or alkaline earth metal oxides, e.g. calcium hydroxide. Suitable salts are any non-toxic, i.e. physiologically safe, salts. They include, above all, the alkali metal salts, e.g. the potassium salts and especially the sodium salts, the ammonium salts and the alkaline earth metal salts, especially the calcium salt. Further appropriate cations for the salts can, where required, be selected by those skilled in the art, since the cations must, as stated above, be non-toxic and give water-soluble salts, and these properties of particular metal cations are well-known or can, as far as solubility in water is concerned, be determined by simple experiments. The above thiophene-saccharins and their non-toxic water-soluble salts are distinguished by exceptional sweetening power, the absence of an after-taste, and non-toxicity.

Amongst the new thienosaccharins, 2,3-dihydro-3-oxothieno[3,4-d]-isothiazole-1,1-dioxide has the greatest sweetening power; it is about 1,000 times as sweet as cane sugar and hence about twice as sweet as saccharin. Accordingly, these compounds are exceptionally suitable for use as artificial sweeteners, for example for sweetening food and drinks and for improving the flavor of drugs. Because of their high sweetening power and their lack of nutritional value the compounds obtainable according to the invention are exceptionally valuable for sweetening foods for diabetics and for persons who tend to adiposity or suffer from intestinal complaints. The compounds can also be used as animal feed ingredients.

However, the synthesis of the thiophene-saccharins by conventional methods was not yet entirely satisfactory in respect of simple and economical operation, yield and space-time yield of end product, due to the large number of synthesis steps, described above, especially where the manufacture of the 3-chlorosulfonyl-thiophene-4-carboxylic acid compounds and 3-chlorosulfonylthiophene-2-carobxylic acid compounds was concerned.

We have found that 3-halosulfonylthiophene-carboxylic acid compounds of the formula

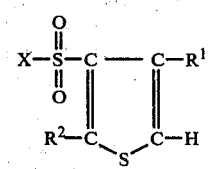

where $R^1$ is

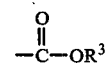

or hydrogen, $R^2$ is hydrogen if $R^1$ is

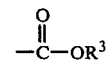

or $R^2$ is

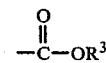

if $R^1$ is hydrogen, $R^3$ is an aliphatic radical or hydrogen and X is halogen are obtained in an advantageous manner if, in a first step, a 3-ketothiophane-carboxylic acid compound of the formula

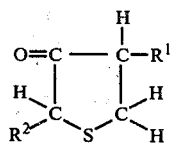

where $R^1$ and $R^2$ have the above meanings, is reacted with a sulfonic acid compound of the formula

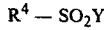   III where $R^4$ is an aliphatic or aromatic radical, Y is halogen or $-OR^3$ or

and $R^3$ has the above meaning, and the resulting 3-sulfato-dihydrothiophene-carboxylic acid compound of the formula

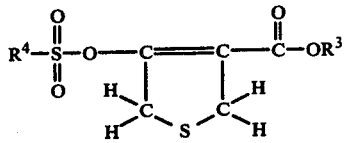
IVa or

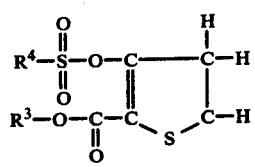
IVb where $R^3$ and $R^4$ have the above meanings, is reacted, in a second step, with an alkali metal polysulfide, whereupon the resulting polysulfido-(3,3')-bis-[dihydrothiophene-carboxylic acid compound] of the formula

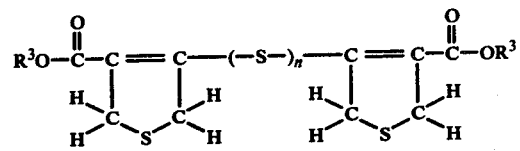
Va or

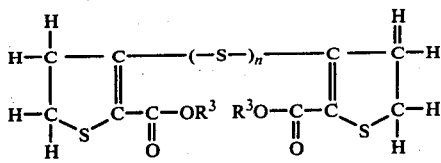
Vb where $R^3$ has the above meaning and n is 2 or an integer greater than 2, is reacted in a third step with a chloride or bromide of sulfuric acid or with chlorine and the resulting polysulfido-(3,3')-bis-[thiophene-carboxylic acid compound] of the formula

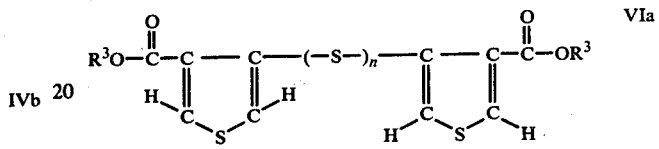
VIa or

VIb where $R^3$ and n have the above meanings, is reacted, in a fourth step, with halogen and water.

Where 3-ketothiophane-4-carboxylic acid methyl ester or 3-ketothiophane-2-carboxylic acid methyl ester, p-toluene-sulfonic acid, sodium disulfide and chlorine are used, the reaction can be represented by the following equations:

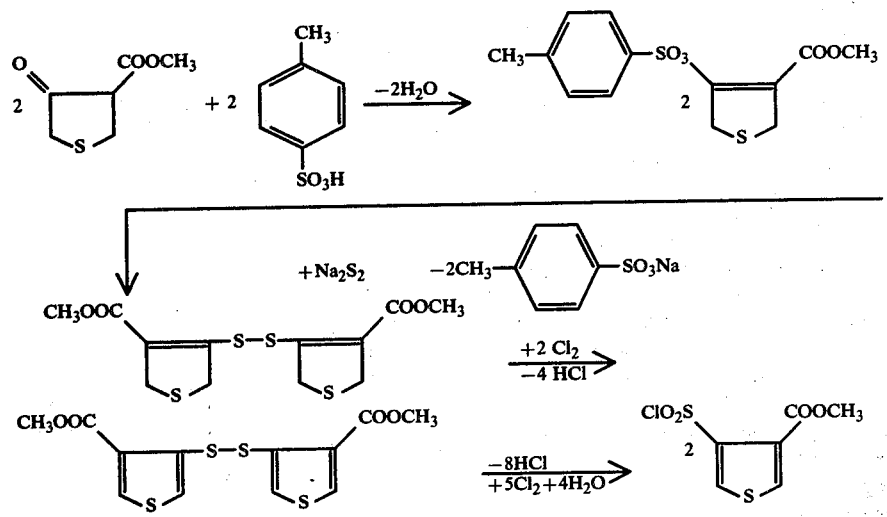

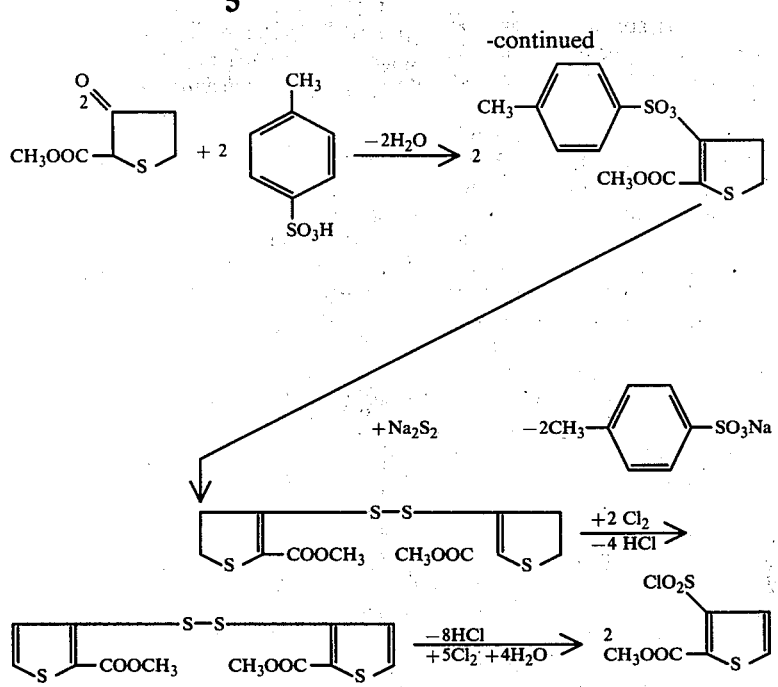

Compared to the conventional processes, the process according to the invention surprisingly gives 3-halosulfonylthiophene-4-carboxylic acid compounds and 3-halosulfonylthiophene-2-carboxylic acid compounds more simply and more economically, in better yield, better space-time yield and greater purity. Involved, multi-stage synthesis operations and purification operations are avoided. It is thus possible, using readily obtainable starting materials, to manufacture thiophene-saccharins more simply, several synthesis operations and working-up operations being eliminated; substantial amounts of solvent, catalyst and auxiliaries are saved or replaced by more easily accessible materials.

The starting compounds II can be obtained in the conventional manner, for example from α,β-unsaturated carboxylic acids or their esters by reaction with thioglycollic acid esters (U.S. Pat. No. 3,445,473, J.Amer.Chem.Soc., 68 (1946), 2,229–2,235, Monatsh. Chemie 104 (1973), 1,520–1,525) or by reaction of 3-oxo-tetrahydro-thiophenes (Organic Reactions VI, 443–468) or their enolate salts with suitable acylating reagents, e.g. acid anhydrides. Preferred starting materials II and compounds III, IV, V and VI, and accordingly preferred end products I are those where $R^1$ is

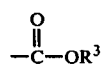

or hydrogen, $R^2$ is hydrogen if $R^1$ is

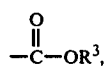

or is

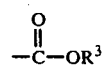

if $R^1$ is hydrogen, $R^3$ and $R^4$ are identical or different and each is alkyl of 1 to 7 carbon atoms, $R^3$ may also be hydrogen, $R^4$ may also be phenyl or alkylphenyl of 7 to 12 carbon atoms, X is chlorine or bromine, Y is chlorine, bromine, hydroxyl, alkoxy of 1 to 7 carbon atoms or

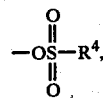

where $R^4$ has the above preferred meaning, and n is an integer from 2 to 9, especially from 2 to 8, advantageously from 2 to 5 and preferably 2. The 3-oxo-tetrahydro compound (3-keto-thiophane compound) II may also be used in the form of the tautomeric 3-hydroxy compound II

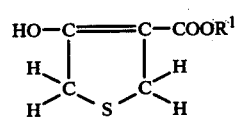

or

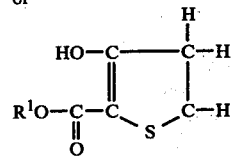

The above radicals may be substituted by groups or atoms which are inert under the reaction conditions, e.g. carbalkoxy of 2 to 4 carbon atoms, alkyl or alkoxy each of 1 to 4 carbon atoms, hydroxyl (as a substituent of phenyl), chlorine (as a substituent of phenyl) and carboxyl (as a substituent of phenyl).

In the 1st stage, starting compound III can be reacted with starting compound II in the stoichiometric ratio or in excess. In general, from 1 to 2, preferably from 1 to 1.1, moles of sulfonic acid compound III are used per mole of starting compound II.

Advantageous sulfonic acid compounds III are monoalkanesulfonic acids of 1 to 6 carbon atoms, especially methanesulfonic acid, ethanesulfonic acid, propane-1-sulfonic acid, n-butane-1-sulfonic acid, n-pentane-1-sulfonic acid and n-hexane-1-sulfonic acid, haloalkanesulfonic acids of 1 to 6 carbon atoms, especially 2-chloroethane-1-sulfonic acid, 2-bromo-1-ethanesulfonic acid, 3-chloropropane-1-sulfonic acid, 3-chlorobutane-1-sulfonic acid, 4-chlorobutane-1-sulfonic acid, 1-chlorobutane-3-sulfonic acid and 1-chlorobutane-4-sulfonic acid, perfluoroalkanesulfonic acids of 1 to 6 carbon atoms, especially perfluoromethanesulfonic acid, perfluoroethanesulfonic acid, perfluoropropane-1-sulfonic acid, perfluorobutane-1-sulfonic acid, perfluoropentane-1-sulfonic acid and perfluorohexane-1-sulfonic acid, benzenesulfonic acids, especially benzenemonosulfonic acid, 2-methylbenzenesulfonic acid, 3-methylbenzenesulfonic acid, 4-methylbenzenesulfonic acid, 2,4-dimethylbenzenesulfonic acid, 2,5-dimethylbenzenesulfonic acid, 2,4,5-trimethylbenzenesulfonic acid, 4-isopropylbenzenesulfonic aicd, 4-n-octylbenzenesulfonic acid and 4-dodecylbenzenesulfonic acid, partially hydrogenated aromatic sulfonic acids, e.g. indan-5-sulfonic acid and tetralin-2-sulfonic acid, carboxybenzenesulfonic acids, halobenzenesulfonic acids and hydroxybenzenesulfonic acids, especially 2-carboxybenzenesulfonic acid, 3-carboxybenzenesulfonic acid, 4-carboxybenzenesulfonic acid, 3,5-dicarboxybenzenesulfonic acid, 3,4-dicarboxybenzenesulfonic acid, 2-chloro-5-carboxybenzenesulfonic acid, 3-chloro-4-carboxybenzene-sulfonic acid, 4-chlorobenzenesulfonic acid, 3-chlorobenzenesulfonic acid, 2-chlorobenzenesulfonic acid, 2,5-dichlorobenzenesulfonic acid, 3,4-dichlorobenzenesulfonic acid, 2,4,5-trichlorobenzenesulfonic acid, 2-hydroxybenzenesulfonic acid, 3-hydroxybenzenesulfonic acid, 4-hydroxybenzenesulfonic acid, 3-chloro-4-methylbenzenesulfonic acid, 5-chloro-2-methylbenzenesulfonic acid, 4-chloro-3-methylbenzenesulfonic acid, 3-chloro-4-hydroxybenzenesulfonic acid and 5-chloro-2-hydroxybenzenesulfonic acid, polynuclear aromatic sulfonic acids, especially benzophenone-4-sulfonic acid, diphenylmethane-4-sulfonic acid, diphenylsulfone-3-sulfonic acid, naphthalene-1-sulfonic acid, naphthalene-2-sulfonic acid, diphenyl ether-4-sulfonic acid, acenaphthene-3-sulfonic acid and acenaphthene-5-sulfonic acid, corresponding sulfonic acid chlorides and bromides, the methyl, ethyl, n-propyl, isopropyl, n-butyl, isobutyl, sec.-butyl, tert.-butyl, pentyl and hexyl esters of the above sulfonic acids and corresponding sulfonic acid anhydrides; methanesulfonic acid chloride, p-toluenesulfonic acid chloride, benzenesulfonic acid chloride, p-toluenesulfonic anhydride and benzenesulfonic anhydride are preferred.

Examples of suitable starting materials II are 4-ethoxycarbonyl-, 4-methoxycarbonyl-, 4-n-butoxycarbonyl-, 4-tert.-butoxycarbonyl-, 4-sec.-butoxycarbonyl-, 4-propoxycarbonyl-, 4-isobutoxycarbonyl-, 4-isopropoxycarbonyl-, 4-pentoxycarbonyl-, 4-heptyloxycarbonyl-, and 4-hexoxycarbonyl-3-hydroxy-dihydrothiophene, and 2-carboxy-, 2-ethoxycarbonyl-, 2-methoxycarbonyl-, 2-n-butoxycarbonyl-, 2-tert.-butoxycarbonyl-, 2-sec.-butoxycarbonyl, 2-propoxycarbonyl-, 2-isobutoxycarbonyl-, 2-isopropoxycarbonyl-, 2-pentoxycarbonyl-, 2-heptyloxycarbonyl- and 2-hexoxycarbonyl-3-hydroxy-dihydrothiophene.

Advantageously, the 1st stage is carried out in the presence of an acid-binding agent, generally used in stoichiometric amount or in excess, advantageously in an amount of from 1 to 1.1 equivalents per mole of starting material II. Preferred acid-binding agents are tertiary amines, alkaline earth metal compounds, ammonium compounds and especially alkali metal compounds, and corresponding mixtures. Advantageous alkali metal compounds and alkaline earth metal compounds are the hydroxides, oxides, carbonates, bicarbonates, salts of weak or polybasic acids and alcoholates of calcium, barium, magnesium, lithium and especially sodium and potassium. Specific examples of basic compounds are potassium hydroxide, sodium hydroxide, potassium carbonate, sodium carbonate, potassium bicarbonate, calcium hydroxide, barium oxide, magnesium hydroxide, calcium carbonate, sodium acetate, propionate, ethyleneglycollate, methylate, propylate, isopropylate, ethylate and tripropyleneglycollate, potassium tert.-butylate, trimethylamine, triethylamine, pyridine, diethylaniline, dimethylaminoethanol, N-ethylpiperidine, N-methylpyrrolidine, dimethylaniline, quinoline and N-methylpyrrolidone. Basic ion exchangers may also be used to bind the acid.

The reaction of the first stage is as a rule carried out at from $-20°$ to $+200°$ C., preferably from $-10°$ to $+10°$ C., under reduced pressure or superatmospheric pressure or, preferably, at atmospheric pressure, continuously or batchwise. Advantageously, one of the reactants, preferably a tertiary amine, e.g. pyridine, is used as the solvent medium; if required, however, organic solvents which are inert under the reaction conditions, such as aromatic hydrocarbons, e.g. toluene, ethylbenzene, o-, m- and p-xylene, isopropylbenzene and methylnaphthalene, alkanols and cycloalkanols, e.g. ethanol, methanol, n-butanol, isobutanol, tert.-butanol, glycol, n-propanol, isopropanol, amyl alcohol, cyclohexanol, 2-methyl-4-pentanol, ethylene glycol monoethyl ether, 2-ethylhexanol, methylglycol, n-hexanol, isohexanol, isoheptanol, n-heptanol and ethylbutanol, and corresponding mixtures, are used. The solvent is advantageously used in an amount of from 200 to 10,000 percent by weight, preferably from 400 to 2,000 percent by weight, based on starting material II.

The reaction may be carried out as follows: a mixture of starting material II, starting material III and, advantageously, a solvent and/or basic compound is kept at the reaction temperature for from 5 to 15 hours. Compound IV, i.e. IVa or IVb, is then isolated from the mixture in the conventional manner, for example by fractional distillation.

In the second reaction step, the 3-sulfato-dihydrothiophenecarboxylic acid compounds IV, obtained as above, are reacted with the alkali metal polysulfide in the stoichiometric amount or in excess, preferably using a ratio of from 0.5 to 1.0, especially from 0.5 to 0.6, mole of polysulfide per mole of compound IV. As regards the manufacture of polysulfides, reference may be made to Ullmanns Encyklopädie der technischen Chemie, Volume 15, pages 527–530. It is advantageous to use potassium polysulfide and especially sodium polysulfide, especially of 2 to 8, advantageously of 2 to 5, sulfur atoms. Potassium disulfide and sodium disulfide are preferred. The reaction in the 2nd step is as a rule carried out at from $-30°$ to $+100°$ C., preferably from $-10°$ to $+30°$ C., under reduced or superatmospheric pressure or preferably at atmospheric pressure, continuously or batchwise. Water is a suitable solvent and is advantageously used in the form of the aqueous polysulfide solution, polysulfide suspension or polysulfide dispersion. An advantageous amount is from 0 to 100, preferably from 0 to 60, percent by weight of water, based on starting material II. Organic solvents which are inert under the reaction conditions, e.g. dimethylformamide, N-methylpyrrolidone, dimethylsulfoxide, and mixtures thereof, may also be used. The organic solvent is advantageously used in an amount of from 200 to 10,000 percent by weight, preferably from 400 to 1,000 percent by weight, based on starting material II.

The reaction of the 2nd step may be carried out as follows: a mixture of compound IV, polysulfide, water and/or solvent is kept at the reaction temperature for from 0.5 to 8 hours. Compound V, i.e. Va or Vb, is then isolated from the mixture in the conventional manner, for example by extracting with a solvent, e.g. methylene chloride, washing with water, drying and distilling.

In step 3, the compound V is reacted with the dehydrogenating agent according to the invention in the stoichiometric amount or in excess, preferably using from 1 to 2, especially from 1 to 1.1, equivalents of dehydrogenating agent per mole of starting compound V. The dehydrogenating agents are sulfuryl chloride, sulfuryl bromide and chlorine. The reaction of the 3rd step is as a rule carried out at from $-20°$ to $+100°$ C., preferably from $-10°$ to $+30°$ C., under reduced pressure or superatmospheric pressure or preferably at atmospheric pressure, continuously or batchwise. Advantageously, solvents which are inert under the reaction conditions are used. Examples of suitable solvents are aromatic hydrocarbons, e.g. toluene, ethylbenzene, o-, m- and p-xylene, isopropylbenzene and methylnaphthalene, halohydrocarbons, especially chlorohydrocarbons, e.g. tetrachloroethylene, 1,1,2,2- or 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- or 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and iso-butyl chloride, chlorobenzene, fluorobenzene, bromobenzene, iodobenzene, o-, p- and m-dichlorobenzene, o-, p-, and m-dibromobenzene, o-, m-, and p-chlorotoluene, 1,2,4-trichlorobenzene, 1,10-dibromodecane and 1,4-dibromobutane, ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether, aliphatic or cycloaliphatic hydrocarbons, e.g. heptane, pinane, nonane, gasoline fractions within the boiling range of from 70° to 190° C., cyclohexane, methylcyclohexane, petroleum ether, decalin, pentane, hexane, naphtha, 2,2,4-trimethylpentane, 2,2,3-trimethylpentane, 2,3,3-trimethylpentane and octane, dimethylformamide, and mixtures thereof. Advantageously, the solvent is used in an amount of from 200 to 10,000 percent by weight, preferably from 400 to 2,000 percent by weight, based on starting compound II or V. At times it is advantageous to carry out the reaction under exposure to a light source of from 2,000 to 8,000 Å. Assistants, e.g. azo-bis-isobutyronitrile, advantageously in an amount of from 1 to 5 percent by weight, based on starting compound II or V, may also be added. The reaction is advantageously carried out in the presence of an acid-binding agent; for this purpose, the amounts and/or compounds specified for the 1st step of the reaction, and in particular the advantageous amounts and compounds specified, may be used.

The reaction of the 3rd step may be carried out as follows: a mixture of compound V and dehydrogenating agent, with or without solvent and/or acid-binding agent, is kept at the reaction temperature for from 0.5 to 3 hours. The end product VI, i.e. VIa or VIb, is then isolated from the mixture in the conventional manner, e.g. by extracting with one of the above solvents or washing with alkali, e.g. a sodium bicarbonate solution, and distilling the organic phase.

The polysulfido-(3,3')-bis-[thiophene-carboxylic acid compound] VIa or VIb, thus obtained, is reacted with halogen and/or water in the stoichiometric amount or in excess, preferably in a ratio of from 5 to 10, especially from 5 to 6, moles of halogen per mole of compound II or VI and/or of from 4 to 100, especially from 4 to 20, moles of water per mole of compound II or VI. The preferred halogens are bromine, iodine and especially chlorine. The reaction is as a rule carried out at from $-30°$ to $+100°$ C., preferably from $-10°$ to $+10°$ C., under reduced pressure or superatmospheric pressure or preferably at atmospheric pressure, continuously or batchwise. Advantageously, organic solvents which are inert under the reaction conditions are used, such as the solvents already described in connection with the 3rd step of the process; more particularly, the above general and preferred amounts, groups of solvents and/or individual solvents are used. At times it is advantageous to carry out the reaction under exposure to a light source of from 2,000 to 8,000 Å. Assistants, e.g. azo-bis-isobutyronitrile, advantageously in an amount of from 1 to 5 percent by weight, based on starting compound II or VI, may also be added.

The reaction of the 4th step can be carried out as follows: a mixture of compound VI, water and halogen, with or without solvent, is kept at the reaction temperature for from 0.5 to 3 hours. The end product is the isolated from the mixture in the conventional manner, e.g. by removing the organic phase of the reaction mixture and carrying out a fractional distillation.

The thiophene compounds which may be manufactured by the process of the invention are valuable starting materials for the manufacture of drugs (Belgian Pat. No. 832,707), dyes and crop protection agents and have an anti-inflammatory, analgesic and anti-rheumatic action. All end products with the above preferred meanings of the various radicals are particularly suitable for this purpose. Regarding their use, reference may be made to the above literature and to Ullmanns Encyklopädie der technischen Chemie, Volume 17, page 354. In particular, the end products I may be used as starting materials for the manufacture of sweeteners which are non-toxic and free from after-taste, flavor-improving auxiliaries, diabetic aids and feedstuffs, and provide the possibility of a simple and economical synthesis of thiophenesaccharins.

In the Examples which follow, parts are by weight and bear the same relation to parts by volume as that of the kilogram to the liter.

EXAMPLE 1 a. 3-p-Toluenesulfato-dihydrothiophene-4-carboxylic acid methyl ester

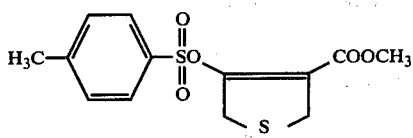

160 parts of 3-hydroxydihydrothiophene-4-carboxylic acid methyl ester and 210 parts of p-toluenesulfonyl chloride are dissolved in 500 parts by volume of pyridine at 0° C. The solution is stirred at 5° C. for 15 hours. After the reaction, the mixture is poured into 1,000 parts by volume of ice water and is stirred for a further 30 minutes. The end product is filtered off and dried at 30° C. 300 parts (96% of theory) of 3-p-toluenesulfato-dihydrothiophene-4-carboxylic acid methyl ester of melting point 81°–83° C. (after recrystallization from cyclohexane) are obtained.

b. Disulfido-(3,3')-bis-(dihydrothiophene-4-carboxylic acid methyl ester)

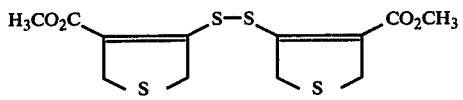

50 parts by volume of dimethylformamide and 9.42 parts of 3-p-toluenesulfato-dihydrothiophene-4-carboxylic acid methyl ester are mixed and 3.3 parts of disodium disulfide . 5 H₂O are added in portions over one hour, at from 20° to 25° C. The mixture is stirred for 8 hours at 0° C., diluted with 200 parts by volume of methylene chloride and introduced into 200 parts of ice/water. The organic phase is separated off, washed with five times 200 parts by volume of water, dried over sodium sulfate, filtered off and concentrated. The residue is recrystallized from toluene. 5.25 parts (75% of theory) of disulfido-(3,3')-bis-(dihydrothiophene-4-carboxylic acid methyl ester) of melting point 182°–186° are obtained.

c. Disulfido-(3,3')-bis-(thiophene-4-carboxylic acid methyl ester)

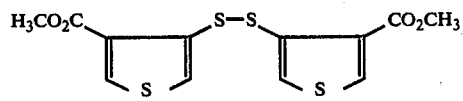

50 parts by volume of methylene chloride and 3.5 parts of disulfido-(3,3')-bis-(dihydrothiophene-4-carboxylic acid methyl ester) are mixed and 1.62 parts of sulfuryl chloride are added in the course of 15 minutes at from 20° to 25° C. The reaction mixture is stirred for 30 minutes at 23° C. and is then diluted with 50 parts by volume of methylene chloride, washed with three times 100 parts by volume of water, dried over sodium sulfate, filtered off and concentrated. 3.39 parts (98% of theory) of disulfido-(3,3')-bis-(thiophene-4-carboxylic acid methyl ester) of melting point 92°–95° C. are obtained.

d. 3-Chlorosulfonylthiophene-4-carboxylic acid methyl ester

34.6 parts of disulfido-(3,3')-bis-(thiophene-4-carboxylic acid methyl ester) are dissolved in a mixture of 300 parts of chloroform and 30 parts of water. 43 parts of chlorine are passed in over 30 minutes at from 0° to 5° C. The mixture is then stirred for 2 hours at 3° C. The organic phase is separated off, dried and concentrated. The oily residue crystallizes and is recrystallized from carbon tetrachloride. 22.1 parts (92% of theory) of 3-chlorosulfonylthiophene-4-carboxylic acid methyl ester of melting point 70°–72° C. are obtained.

EXAMPLE 2 a. (Preparation of compound IV): 3-Methylsulfonato-dihydrothiophene-2-carboxylic acid methyl ester

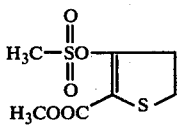

16 parts of 3-ketothiophane-2-carboxylic acid methyl ester and 8.6 parts by volume of methanesulfonic acid chloride are dissolved in 100 parts by volume of pyridine at 0° C. The solution is stirred for 15 hours at 5° C. After the reaction, the mixture is added to 150 parts by volume of ice/water and is extracted three times with 50 parts by volume of methylene chloride. The combined organic phases are washed twice with 50 parts by volume of 10 percent strength by weight aqueous citric acid solution and three times with saturated, aqueous sodium chloride solution. After drying and concentrating the organic phases, 18.8 parts (79% of theory) of 3-methylsulfonato-dihydrothiophene-2-carboxylic acid methyl ester of melting point 75°–77° C. are obtained.

b. (Preparation of compound V): Disulfido-(3,3')-bis-(dihydrothiophene-2-carboxylic acid methyl ester)

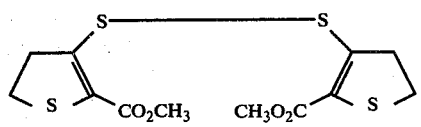

50 parts by volume of dimethylformamide and 9.52 parts of 3-methylsulfonato-dihydrothiophene-2-carboxylic acid methyl ester are mixed. 3.3 parts of disodium disulfide (containing 5 moles of water of crystallization per mole) are added in portions over one hour at from 20° to 25° C. The mixture is stirred for 6 hours at 0° C., diluted with 200 parts by volume of methylene chloride and added to 200 parts of ice/water. The organic phase is separated off, washed with five times 200 parts by volume of water, dried with sodium sulfate, filtered off and concentrated. The residue is recrystallized from toluene. 5.25 parts (75% of theory) of disulfido-(3,3')-bis-dihydrothiophene-2-carboxylic acid methyl ester) of melting point 133°–137° C. are obtained.

c. (Preparation of compound VI): Disulfido-(3,3')-bis-(thiophene-2-carboxylic acid methyl ester)

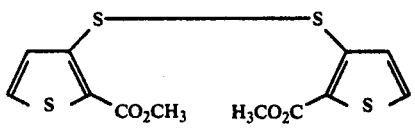

50 parts by volume of methylene chloride and 3.5 parts of disulfido-(3,3')-bis-(dihydrothiophene-2-carboxylic acid methyl ester) are mixed. 1.62 parts by volume of sulfuryl chloride are added over 15 minutes at 23° C. The reaction mixture is then stirred for 30 minutes at 23° C., diluted with 50 parts by volume of methylene chloride, washed with three times 100 parts of volume of water, dried over sodium sulfate, filtered off and concentrated. 3.39 parts (98% of theory) of disulfido-(3,3')-bis-(thiophene-2-carboxylic acid methyl ester) of melting point 144°–145° C. are obtained.

d. (Reaction): 3-Chlorosulfonylthiophene-2-carboxylic acid methyl ester

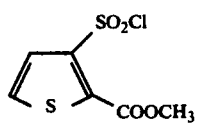

34.6 parts of disulfido-(3,3')-bis-(thiophene-2-carboxylic acid methyl ester) are dissolved in a mixture of 300 parts of carbon tetrachloride and 30 parts of water. 43 parts of $Cl_2$ are passed in over 1.5 hours at 3° C. Thereafter the mixture is stirred for two hours at 3° C. The organic phase is separated off, dried and concentrated. The oily residue crystallizes and is recrystallized from carbon tetrachloride. 22.1 parts (92% of theory) of 3-chloro-sulfonylthiophene-2-carboxylic acid methyl ester of melting point 60°–62° C. are obtained.

We claim:

1. A process for the manufacture of a 3-halosulfonyl-thiophene-carboxylic acid compounds of the formula

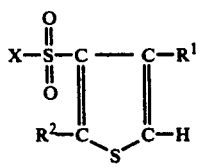

I where $R^1$ is

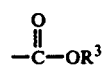

or hydrogen, $R^2$ is hydrogen if $R^1$ is

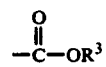

or $R^2$ is

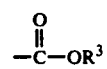

if $R^1$ is hydrogen, $R^3$ is an aliphatic radical or hydrogen and X is halogen, wherein, in a first step, a 3-ketothiophane-carboxylic acid compound of the formula

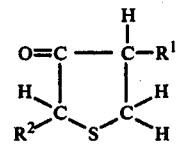

II where $R^1$ and $R^2$ have the above meanings, is reacted with a sulfonic acid compound of the formula $$R^4 - SO_2Y$$

III where $R^4$ is an aliphatic or aromatic radical, Y is halogen or $-OR^3$ or

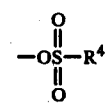

and $R^3$ has the above meaning, and the resulting 3-sulfato-dihydrothiophene-carboxylic acid compound of the formula

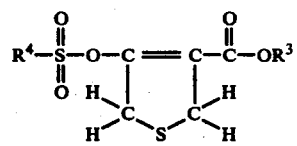

IVa or

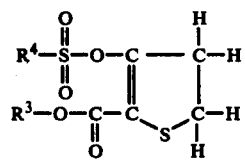

IVb where $R^3$ and $R^4$ have the above meanings, is reacted, in a second step, with an alkali metal polysulfide, whereupon the resulting polysulfido-(3,3')-bis-[dihydrothiophene-carboxylic acid compound] of the formula

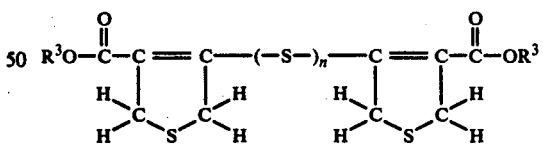

Va or

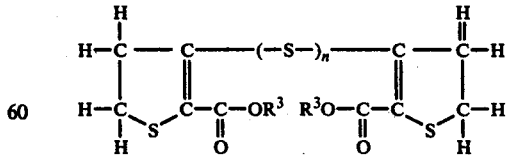

Vb where $R^3$ has the above meaning and n is 2 or an integer greater than 2, is reacted in a third step with a chloride or bromide of sulfuric acid or with chlorine and the resulting polysulfido-(3,3')-bis-[thiophene-carboxylic acid compound] of the formula

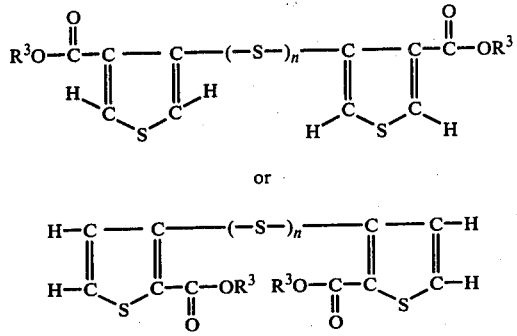

where $R^3$ and n have the above meanings, is reacted, in a fourth step, with halogen and water.

2. A process as claimed in claim 1, wherein the reaction in the first step is carried out with from 1 to 2 moles of sulfonic acid compound III per mole of starting compound II.

3. A process as claimed in claim 1, wherein the reaction in the first step is carried out in the presence of an acid-binding agent.

4. A process as claimed in claim 1, wherein the reaction in the first step is carried out at from $-20°$ to $+200°$ C.

5. A process as claimed in claim 1, wherein the reaction in steps 1, 3 and 4 is carried out in the presence of from 200 to 10,000 percent by weight, based on starting compound II, of an organic solvent which is inert under the reaction conditions.

6. A process as claimed in claim 1, wherein the reaction in the 2nd step is carried out with a ratio of from 0.5 to 1.0 mole of polysulfide per mole of compound IV.

7. A process as claimed in claim 1, wherein the reaction in the 2nd step is carried out with potassium polysulfide or sodium polysulfide of 2 to 8 sulfur atoms.

8. A process as claimed in claim 1, wherein the reaction in the 2nd step is carried out at from $-30°$ to $-100°$ C.

9. A process as claimed in claim 1, wherein the reaction in the 2nd step is carried out with from 0 to 100 percent by weight of water, based on starting compound II.

10. A process as claimed in claim 1, wherein the reaction in the 3rd step is carried out with from 1 to 2 equivalents of dehydrogenating agent per mole of starting compound V.

11. A process as claimed in claim 1, wherein the reaction in the 3rd step is carried out at from $-20°$ to $+100°$ C.

12. A process as claimed in claim 1, wherein the reaction in the 4th step is carried out with a ratio of from 5 to 10 moles of halogen per mole of compound VI.

13. A process as claimed in claim 1, wherein the reaction in the 4th step is carried out with from 4 to 100 moles of water per mole of compound VI.

14. A process as claimed in claim 1, wherein the reaction in the 4th step is carried out at from $-30°$ to $+100°$ C.

* * * * *